(12) United States Patent
Melzig et al.

(10) Patent No.: US 8,933,220 B2
(45) Date of Patent: Jan. 13, 2015

(54) PHOTOCHROMIC FUSED NAPHTHOPYRANS HAVING A BENZENE RING WHICH IS ADJACENT TO THE PYRAN OXYGEN AND IS LINKED TO THE PARA SUBSTITUENT VIA BOTH META POSITIONS

(75) Inventors: Manfred Melzig, Wessling (DE); Yven Rohlfing, München (DE); Udo Weigand, München (DE)

(73) Assignee: Rodenstock GmbH, München (DE)

( * ) Notice: Subject to any disclaimer, the term of this patent is extended or adjusted under 35 U.S.C. 154(b) by 0 days.

(21) Appl. No.: 13/996,895

(22) PCT Filed: Dec. 21, 2011

(86) PCT No.: PCT/EP2011/006479
§ 371 (c)(1),
(2), (4) Date: Aug. 5, 2013

(87) PCT Pub. No.: WO2012/084231
PCT Pub. Date: Jun. 28, 2012

(65) Prior Publication Data
US 2013/0310556 A1    Nov. 21, 2013

(30) Foreign Application Priority Data
Dec. 23, 2010  (DE) .......................... 10 2010 055 760

(51) Int. Cl.
| | | |
|---|---|---|
| C07D 223/14 | (2006.01) | |
| C07D 221/18 | (2006.01) | |
| G02B 5/23 | (2006.01) | |
| C07D 311/92 | (2006.01) | |

(52) U.S. Cl.
CPC ................ *G02B 5/23* (2013.01); *C07D 311/92* (2013.01)

USPC .............................................. 540/581; 546/72

(58) Field of Classification Search
USPC ........................................... 540/581; 546/72
See application file for complete search history.

(56) References Cited

U.S. PATENT DOCUMENTS

| | | |
|---|---|---|
| 3,567,605 A | 3/1971 | Becker |
| 5,645,767 A | 7/1997 | Gemert |
| 5,698,141 A | 12/1997 | Kumar |
| 5,723,072 A | 3/1998 | Kumar |
| 5,955,520 A | 9/1999 | Heller et al. |
| 6,018,059 A | 1/2000 | Chan et al. |
| 6,225,466 B1 | 5/2001 | Mann et al. |
| 6,858,732 B2 | 2/2005 | Qin et al. |
| 2011/0081482 A1 | 4/2011 | Melzig et al. |
| 2011/0201489 A1 | 8/2011 | Melzig et al. |

FOREIGN PATENT DOCUMENTS

| | | |
|---|---|---|
| EP | 0 987 260 B1 | 5/2001 |
| EP | 1184379 A1 | 3/2002 |
| EP | 1394156 A1 | 3/2004 |
| JP | 2000344762 A | 12/2000 |
| WO | 9614596 A1 | 5/1996 |
| WO | 9832037 A1 | 7/1998 |
| WO | 9915518 A1 | 4/1999 |
| WO | 2009024271 A1 | 2/2009 |
| WO | 2009132842 A1 | 11/2009 |

OTHER PUBLICATIONS

International Search Report for PCT/EP2011/006479 dated Mar. 7, 2012.

*Primary Examiner* — Kristin Vajda
(74) *Attorney, Agent, or Firm* — McDonald Hopkins LLC

(57) ABSTRACT

The present invention relates to photochromic fused naphthopyrans having a benzene ring which is adjacent to the pyran oxygen and is linked to the para substituent via both meta positions, and to the use thereof in plastics of all types, in particular for ophthalmic purposes.

14 Claims, 1 Drawing Sheet

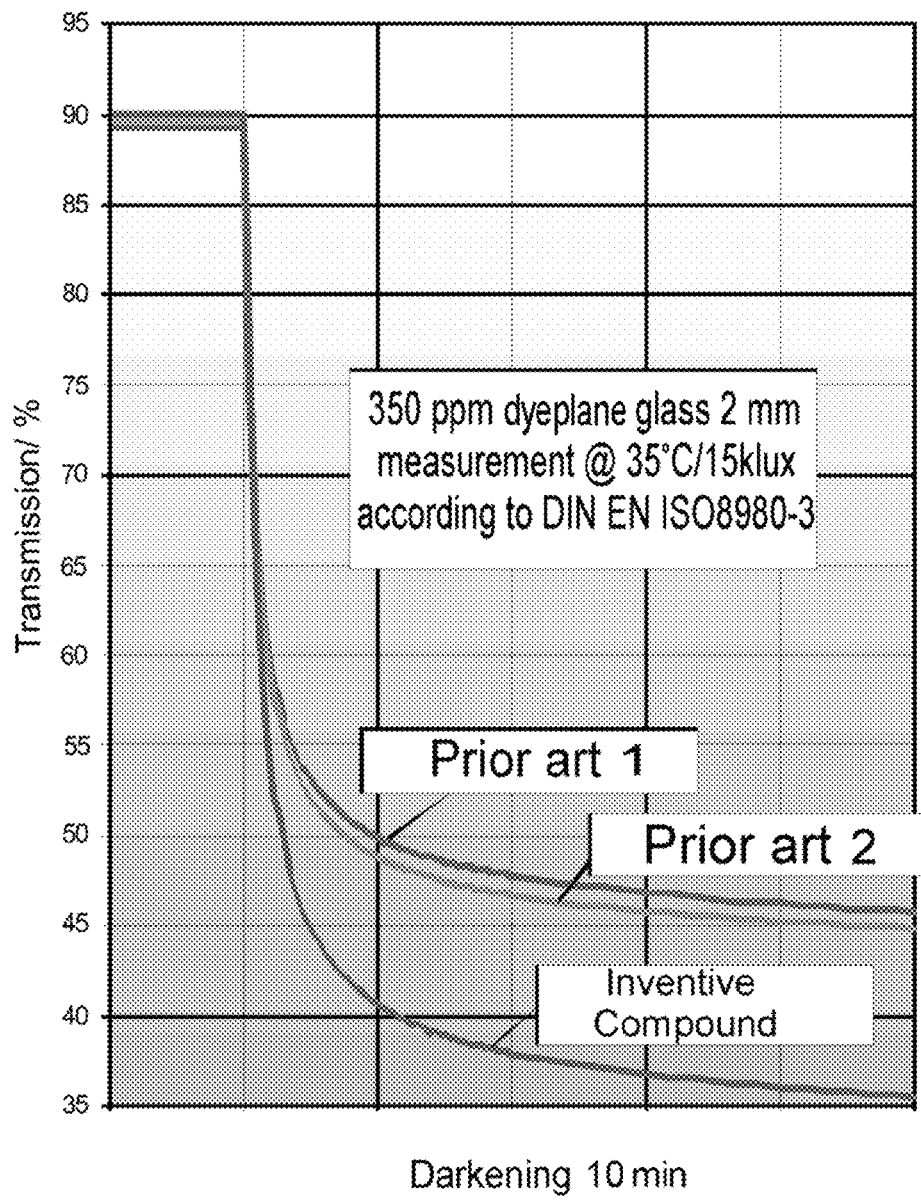

PHOTOCHROMIC FUSED NAPHTHOPYRANS HAVING A BENZENE RING WHICH IS ADJACENT TO THE PYRAN OXYGEN AND IS LINKED TO THE PARA SUBSTITUENT VIA BOTH META POSITIONS

CROSS-REFERENCE TO RELATED APPLICATIONS

This application claims the benefit of International Patent Application No: PCT/EP2011/006479, entitled "Photochromic Anellated Naphthopyrans Having A Benzene Ring Which Is Adjacent To The Pyran Acid And Is Linked To The Para Substituents Via Both Meta Positions" filed on Dec. 21, 2011, and German Application No.: 10 2010 055 760.9, filed on Dec. 23, 2010 which are herein incorporated in their entirety by reference.

FIELD

The present invention relates to photochromic fused naphthopyrans having a benzene ring which is adjacent to the pyran oxygen and is linked to the para substituent via both meta positions, and to the use thereof in plastics of all types, in particular for ophthalmic purposes.

BACKGROUND

Various classes of dyes have long been known that reversibly change their color when irradiated with light of certain wavelengths, particularly sunlight. This is due to the fact that these dye molecules are converted by light energy into an excited state, which they leave again when the energy input is interrupted and they return to their ground state. These photochromic dyes include various pyran systems, which have previously been described in the prior art, having different base systems and substituents.

Pyrans, especially naphthopyrans and larger ring systems derived from these, are currently the most commonly used class of photochromic compounds. Although patented for the first time back in 1966 (U.S. Pat. No. 3,567,605), two pyran compound classes were first developed in the 1990s which are suitable for use in phototropic spectacle lenses. The latter concerns 2,2-diaryl-2H-naphtho[1,2-b]pyrans and 3,3-diaryl-3H-naphtho[2,1-b]pyrans, whose open (excited) forms have various darkening colors from yellow to red-violet.

2,2-Diaryl-2H-naphtho[1,2-b]pyrans having an additional fused attachment on the pyrano-fused benzene ring are of considerable interest, since they absorb longer wavelengths due to their larger ring systems and thus violet and blue darkening colors are accessible. This additional fused attachment is generally a benzene ring (in formula (I) the benzene ring having the substituents $R^2$), which is again bridged in the ortho position to the naphthopyran (see Z in formula (I)).

If this bridge constitutes only one atom, this results in a 5-membered ring fused to the benzopyran. Examples for one carbon atom can be found in U.S. Pat. Nos. 5,645,767, 5,723,072 and 5,955,520 and for one oxygen atom in U.S. Pat. No. 6,018,059.

In U.S. Pat. No. 5,723,072, in addition to this base system, an un-, mono- or disubstituted heterocyclic ring may be fused to the g, h, i, n, o or p side of the indenonaphthopyran. Thus indeno[1,2-f]naphtho[1,2-b]pyrans having a very wide range of possible substituents are disclosed.

WO 96/14596, WO 99/15518, U.S. Pat. No. 5,645,767, WO 98/32037 and U.S. Pat. No. 5,698,141 disclose photochromic indeno-fused naphthopyran dyes derived from 2H-naphtho[1,2-b]pyran, the compositions containing them and a method for the preparation thereof. In U.S. Pat. No. 5,698,141, in addition to this base system, an un-, mono- or disubstituted heterocyclic ring may be fused to the g, h, i, n, o or p side of the indenonaphthopyran. The respective very extensive substituent list also comprises very particular spiro compounds, namely those systems having a spiro heterocyclic group, wherein, including the spiro atom at the 13-position of the base system, a 5- to 8-membered ring is present which always comprises two oxygen atoms. A further embodiment of the spiro ring is found in the Japanese application 344762/2000.

The different photochromic dyes available in the prior art have disadvantages, however, which substantially affect the wear comfort of the spectacles wearer when using sun protection lenses. Firstly, the dyes do not have a sufficiently long-wave absorption in the excited state and in the non-excited state. Secondly, there is often too high a temperature sensitivity of the darkening, and at the same time too slow a brightening can occur. Moreover, the dyes available in the prior art often have an insufficient lifetime and therefore allow only a low service life of the sun protection lenses. The latter manifests itself in rapidly declining performance and/or noticeable yellowing.

The substituents in the position ortho to the pyran oxygen atom are mainly referred to in the prior art only with B and B'. They are mainly aromatic or heteroaromatic substituents. In addition, the substituents B and B'—together form a separate cyclic aliphatic or aromatic or heteroaromatic ring system. Influencing the photochromic properties by suitable selection of the substituents B and B' with the exception of ortho substituents on the benzene ring adjacent to the pyran oxygen is virtually unreported in the prior art. Even small ortho substituents on the benzene ring adjacent to the pyran oxygen, such as fluorine, methyl or methoxy, slow the brightening rate so severely that they cannot be used as intended in spectacle lenses.

It is an object of the present invention to provide a class of novel photochromic compounds having improved properties compared to the structures described in the prior art. These include, inter alia, a very high darkening performance even at elevated temperatures, a rapid brightening rate and a very good light stability.

This problem is solved by the subjects characterized in the claims.

In particular, photochromic naphthopyrans are provided having the general formulae (I) and (II):

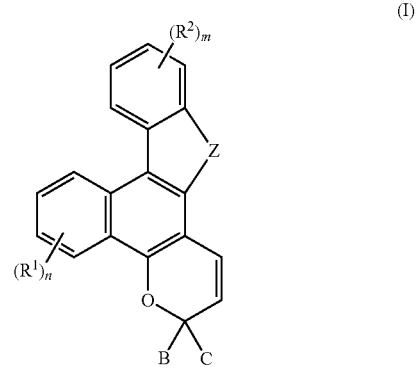

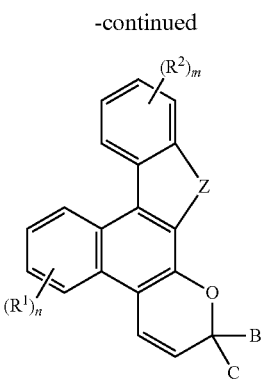

(II)

wherein
the radicals R¹ and R² are each independently a substituent selected from the group α, consisting of a hydrogen atom, a ($C_1$-$C_6$)-alkyl radical, a ($C_1$-$C_6$)-thioalkyl radical, a ($C_3$-$C_7$)-cycloalkyl radical which may have one or more heteroatoms such as O or S, a ($C_1$-$C_6$)-alkoxy radical, an hydroxyl group, a trifluoromethyl group, bromine, chlorine, fluorine, an unsubstituted, monosubstituted or disubstituted phenyl, phenoxy, benzyl, benzyloxy, naphthyl or naphthoxy radical, wherein the substituents in turn may be selected from the group α; or two radicals R¹ and/or two radicals R² each independently form an unsubstituted, monosubstituted or disubstituted benzo, pyrido, benzofuro or benzothieno ring fused to the base structure, the substituents of which may be selected from the group α; Z is selected from —$CR^{10}R^{11}$—, —O—, —S—, —NPh-, —N($C_1$-$C_6$)alkyl, —O—$CR^{10}R^{11}$—, —$CR^{10}R^{11}$—O—, —S—$CR^{10}R^{11}$—, —$CR^{10}R^{11}$—S—, —$CR^{10}R^{11}$—$CR^{10}R^{11}$—, —$CR^{10}$=N— or —$CR^{10}$=$CR^{11}$—, where the substituents $R^{10}$ and $R^{11}$ may be selected from the group α, preferably from a hydrogen atom, a ($C_1$-$C_6$)-alkyl radical, a ($C_3$-$C_7$)-cycloalkyl radical, an un-, mono- or disubstituted phenyl, benzyl or naphthyl radical;

or Z, incorporating the spiro-carbon atom, is a 3- to 8-membered carbomonocyclic or heteromonocyclic ring which may optionally bear one or more substituents from the group α, and to which one to three aromatic or heteroaromatic ring systems may be fused, wherein the ring system(s) are independently selected from the group β consisting of benzene, naphthalene, phenanthrene, pyridine, quinoline, furan, thiophene, pyrrole, benzofuran, benzothiophene, indole and carbazole, which in turn may be substituted with one or more substituents selected from the group α;

or Z, incorporating the spiro-carbon atom, is a 7- to 12-membered carbobicyclic ring or a 7- to 12-membered carbotricyclic ring, which in turn may have one, two, three or four substituents selected from the group α, and wherein
B is selected from one of the following groups a) or b), wherein
a) is a mono-, di- and trisubstituted aryl radical, wherein the aryl radical is phenyl, naphthyl or phenanthryl;
b) is an un-, mono- and disubstituted heteroaryl radical, wherein the heteroaryl radical is pyridyl, furanyl, thienyl, benzofuranyl, benzothienyl, 1,2,3,4-tetrahydrocarbazolyl and julolidinyl;
wherein the substituents of the aryl and heteroaryl radicals in a) and b) are those selected from the group α or the group χ consisting of hydroxy, amino, mono-($C_1$ $C_6$)-alkylamino, di-($C_1$-$C_6$)-alkylamino, and on the phenyl ring un-, mono- or disubstituted phenethenyl, un-, mono- or disubstituted (phenylimino)methylene, un-, mono- or disubstituted (phenylmethylene)imino and un-, mono- or disubstituted mono- and diphenylamino, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono- or disubstituted 1,2,3,4-tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenz[b,f]azepinyl, wherein the substituent(s) in turn may each independently be selected from ($C_1$ $C_6$)-alkyl, ($C_1$-$C_6$)-alkoxy, bromine, chlorine or fluorine;

or wherein two directly adjacent substituents of the aryl and heteroaryl radicals in a) and b) are a V—$(CR^{12}R^{13})_p$—W moiety, where p is 1, 2 or 3, $R^{12}$ and $R^{13}$ may be hydrogen, methyl or phenyl and V and W may independently be oxygen, sulfur, N—($C_1$-$C_6$)-alkyl, N—$C_6H_5$, $CH_2$, $C(CH_3)_2$ or $C(C_6H_5)_2$, wherein two or more adjacent carbon atoms in this V—$(CR^{12}R^{13})_p$—W moiety each independently can also be part of a fused benzo ring system, which in turn may have one or more substituents selected from the group α or the group χ;

and wherein the aryl radical or heteroaryl radical of the group B in the two positions ortho to the point of attachment to the pyran ring has no substituent other than hydrogen,
and wherein C is a substituent of the following structure,

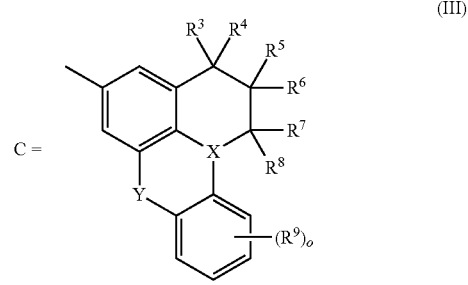

(III)

wherein $R^9$ is defined as $R^1$ and $R^2$, where m, n and o are independently an integer from 1 to 4;
wherein $R^3$ to $R^8$ are each independently a substituent selected from the group α; or
$R^3$ together with $R^4$ or $R^5$ together with $R^6$ or $R^7$ together with $R^8$ independently form, with the respective common carbon atom, a 3- to 8-membered carbomonocyclic or heteromonocyclic ring, which optionally bears one or more substituents from the group α, and to which one to three aromatic or heteroaromatic ring systems may be fused, wherein the ring system(s) are independently selected from the group β consisting of benzene, naphthalene, phenanthrene, pyridine, quinoline, furan, thiophene, pyrrole, benzofuran, benzothiophene, indole and carbazole, which in turn may be substituted with one or more substituents selected from the group α; or four adjacent radicals $R^3$ to $R^6$ or $R^5$ to $R^8$ form an un-, mono- or disubstituted benzo or pyrido ring, fused to the base structure, the substituents of which may be selected from the group α;

where X is N or CR$^{14}$, wherein R$^{14}$ is selected from the group consisting of hydrogen, a (C$_1$-C$_6$)-alkyl radical and un-, mono- and disubstituted phenyl, the substituents of which are selected from the group α; and where Y is O, S, NR$^{15}$, CR$^{15}$R$^{16}$ or CR$^{15}$R$^{16}$—CR$^{15}$R$^{16}$, wherein R$^{15}$ and R$^{16}$ may each be selected as R$^{14}$, or the two radicals R$^{15}$ and R$^{16}$, together with the common carbon atom, form a 3- to 8-membered carbomonocyclic or heteromonocyclic ring, which optionally bears one or more substituents from the group α, and to which one to three aromatic or heteroaromatic ring systems may be fused, wherein the ring system(s) are independently selected from the group β consisting of benzene, naphthalene, phenanthrene, pyridine, quinoline, furan, thiophene, pyrrole, benzofuran, benzothiophene, indole and carbazole, which in turn may be substituted with one or more substituents selected from the group α.

The photochromic fused naphthopyrans are characterized by a benzene ring which is adjacent to the pyran and is linked to the para substituent via both meta positions. The compounds according to the invention are characterized by very high darkening performance even at elevated temperatures, rapid brightening rates and also very good light stabilities. The photochromic fused naphthopyrans according to the invention preferably have the general formula (I) above.

Particularly preferred photochromic fused naphthopyrans according to the present invention, having a benzene ring which is adjacent to the pyran oxygen and is linked to the para substituent via both meta positions, have the following general formulae (III), (IV) and (V):

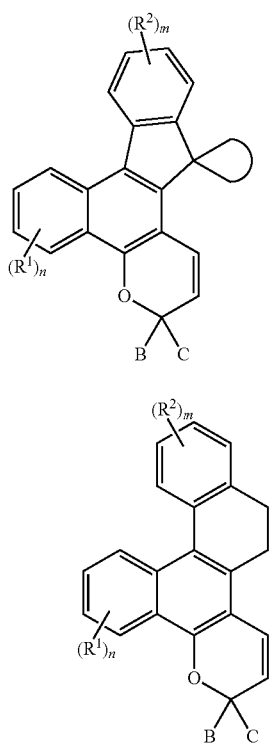

(III)

(IV)

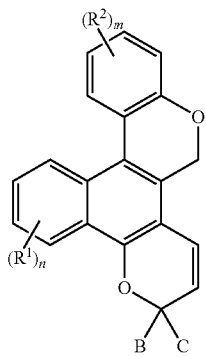

(V)

wherein all radicals are as defined above and wherein the spiro-ring in formula (III), incorporating the spiro-carbon atom, is a 5- to 8-membered carbocyclic ring, which optionally bears one or more substituents from the group α, and to which one to three benzene rings may be fused, which in turn may be substituted with one or more substituents selected from the group α.

In a preferred embodiment of the present invention, the radical B is selected from the group a). In a further embodiment, X is preferably N in the radical C. In the radical C, Y is preferably CR$^{15}$R$^{16}$ or CR$^{15}$R$^{16}$—CR$^{15}$R$^{16}$, wherein R$^{15}$ and R$^{16}$ are as defined previously and are preferably selected from the group consisting of hydrogen, a (C$_1$-C$_6$)-alkyl radical and un-, mono- and disubstituted phenyl, the substituents of which are selected from the group α. The radicals R$^3$ to R$^8$ are preferably each independently a substituent selected from the group α.

In an embodiment of the present invention, the radicals R$^3$ and R$^4$ are each independently a substituent selected from the group α, and the four radicals R$^5$ to R$^8$ together are an un-, mono- or disubstituted benzo or pyrido ring, fused to the base structure, the substituents of which may be selected from the group α

In a particularly preferred embodiment, the radical C has the following structures:

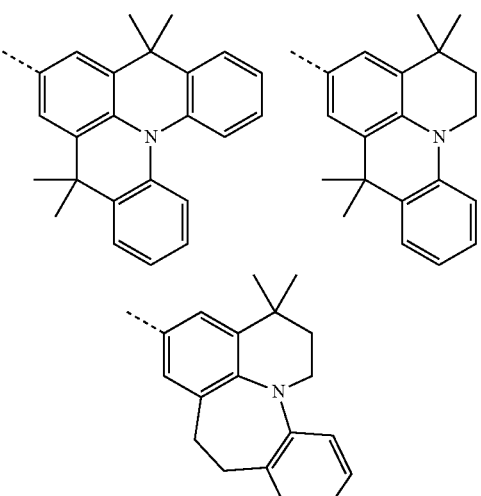

Furthermore, in a further embodiment, two radicals R$^2$ in the above formulae (I)-(V) form an un-, mono- or disubstituted benzo, pyrido, benzofuro or benzothieno ring fused to the base structure, the substituents of which may be selected from the group α. Two radicals R$^2$, mutually in the ortho position, present in the above formulae (I)-(V) are particularly preferably a benzofuro fused attachment.

Z is preferably selected from —$CR^{10}R^{11}$—, —O—$CR^{10}R^{11}$—, —$CR^{10}R^{11}$—O—, —$CR^{10}R^{11}$—$CR^{10}R^{11}$— or —$CR^{10}$=$CR^{11}$—, wherein the substituents $R^{10}$ and $R^{11}$ are selected from the group α, preferably from a hydrogen atom, a ($C_1$-$C_6$)-alkyl radical, a ($C_3$-$C_7$)-cycloalkyl radical, an un-, mono- or disubstituted phenyl, benzyl or naphthyl radical.

BRIEF DESCRIPTION OF THE DRAWINGS

FIG. 1 shows a comparison of the light attenuation properties in the excited state at elevated temperature and weaker light stimulation ("high temperature performance semi-shade") of a compound according to the invention in comparison with compounds from the prior art.

DETAILED DESCRIPTION

A problem of conventional phototropic dyes is an often inadequate high temperature performance, since at elevated temperatures the (thermal) reverse reaction of the excited (colored) form takes place so rapidly that the level of darkening is relatively low. Modern phototropic lenses, however, also demand a sufficient level of darkening at elevated temperatures, namely also in semi-shade with relatively low UV stimulation. Accordingly the kinetikbank measurement at 35° C. and with only 15 klux light stimulation instead of the standard value of 50 klux for full sunlight—is a good measure of the high temperature performance of phototropic dyes. As shown in FIG. 1, compounds according to the invention having the specifically selected substituent C have approximately 10% higher light attenuation at 35° C./15 klux i.e. a 10% lower transmission —in comparison with compounds from the state of the art having analogous naphthopyran subunits and identical dye concentrations.

It was already known that the level of darkening of a photochromic dye in the excited state can be increased if small ortho substituents such as fluorine, methyl or methoxy are placed on the benzene ring adjacent to the pyran oxygen. Although these compounds darken extremely strongly when excited, the brightening rate, however, is thereby so strongly slowed that they cannot be used as intended in spectacle lenses. In contrast to this, the compounds according to the invention, having two meta substituents on the benzene ring adjacent to the pyran oxygen, brighten again very rapidly after complete darkening. The reason lies in the particular structure of the substituent C having a minimum of four fused rings.

Moreover, since the compounds according to the invention have high clarity (i.e. high transmission in the non-excited state) and a very good light stability, they are suitable for use in phototropic lenses, particularly in warmer climate zones, or as an additive for conventional phototropic lenses to increase the level of darkening at relatively high temperatures.

The structure of the compounds used for FIG. 1 from the prior art (from WO2009/024271), and a compound according to the invention, are shown in the following table:

TABLE 1

Structure of a compound according to the invention vs. prior art

| non-excited (colorless) | excited (colored) |
|---|---|

Substituent $(R^2)_m$ = benzofuro fused attachment
(according to WO 2009/024271)
Substituent C in each case is shown below The substituents C of compounds 1 and 2 according to the prior art (from WO2009/024271) and a compound according to the invention are listed below:

C =

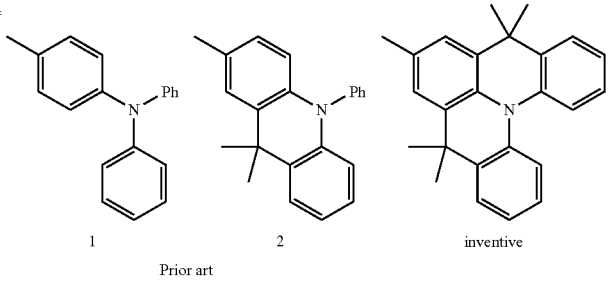

1        2        inventive
Prior art

For measuring the properties of the previously mentioned examples of photochromic dyes according to the invention and the compounds from the prior art (see above), 350 ppm of the dye in each case were dissolved in an acrylate monomer matrix and, after the addition of a polymerization initiator, thermally polymerized by means of a temperature program. The light attenuation and transmission properties of the resulting plastic lenses (2 mm thickness) were then measured according to DIN EN ISO 8980-3.

In Table 2, a comparison, with the prior art, of the intensity of the light attenuation in the excited state (measured directly from the respective longest wavelength absorption maximum) is listed for two further inventive compounds. In the formula, in each case only the substituent C is shown—the rest of the molecule is analogous to the compounds given in Table 1.

TABLE 2

Comparison of the intensity of light attenuation in the excited state (35° C./15 klux); measurement fully darkened directly at the longest wavelength absorption maximum (complete formula see table 1; only substituent C shown)

| Prior art | Inventive compounds | |
|---|---|---|
| [structure] | [structure] | [structure] |
| light attenuation @ 35° C./15 klux | | |
| 58% | 70% | 68% |
| longest wavelength absorption max. | | |
| 590 nm | 610 nm | 590 nm |

The inventive compounds each have an approximately 10% higher light attenuation in the excited state at relatively high temperatures than similar compounds from the prior art.

The preparation of compounds of formula (V), listed in Tables 1 and 2, is carried out analogously to WO 2009/024271, where in the last step the condensation with 2-propyn-1-ol derivatives, which comprise the substituents C selected according to the invention instead of B', is carried out. These can be produced by conventional methods from the appropriately substituted benzophenones. Compounds of the formula (IV) can be synthesized analogously in accordance with WO2009/132842, and the compounds of the formula (III) in accordance with EP 0 987 260.

The compounds according to the invention may be used in plastic materials or plastic items of any type and form for a variety of purposes for which photochromic behavior is of interest. Here, a dye according to the present invention or a mixture of such dyes may be used. For example, the photochromic naphthopyrans according to the invention may be used in lenses, particularly ophthalmic lenses, lenses for spectacles of all types, such as ski goggles, sunglasses, motorcycle goggles, visors of helmets and the like. Furthermore, the photochromic naphthopyrans according to the invention can also be used, for example, as sun protection in vehicles and homes in the form of windows, protective screens, covers, roofs and the like.

For the preparation of such photochromic items, the photochromic naphthopyrans according to the invention can be applied to, or embedded in, a polymeric material, such as an organic plastic material, by various methods described in the prior art, such as already indicated in WO 99/15518.

We distinguish here between so-called mass coloring and surface staining procedures. A mass coloring procedure comprises, for example, the dissolving or dispersing of the photochromic compound or compounds according to the present invention in a plastic material, for example by the addition of the photochromic compound(s) to a monomeric material, before the polymerization is carried out. A further possibility for producing a photochromic article is to permeate the plastic material(s) with the photochromic compound(s) by immersing the plastic material in a hot solution of the photochromic dye(s) according to the present invention or, for example, by a thermal transfer process. The photochromic compound(s) may also be provided, for example, in the form of a separate layer between adjacent layers of the plastic material, for example as part of a polymeric film. Further, it is also possible to deposit the photochromic compound(s) as part of a coating present on the surface of the plastic material. The term "permeation" here is intended to mean the migration of the photochromic compound(s) into the plastic material, for example by the solvent-assisted transfer of the photochromic compound(s) in a polymer matrix, vapor phase transfer or other such surface diffusion processes. Advantageously, such photochromic articles, such as spectacle lenses, can be produced not only by means of conventional mass coloring, but also in the same manner by means of surface staining, where in the latter variant a surprisingly low migration tendency can be achieved. This is a particular advantage in the subsequent processing steps, since—for example, as with an antireflective coating due to the lower back diffusion in a vacuum—delamination and similar defects are drastically reduced.

Overall, based on the photochromic naphthopyrans according to the invention, any compatible (in chemical terms and in a color dependent manner) stains, i.e. dyes, may be applied to, or embedded in, the plastic material in order to satisfy both esthetic aspects and medical or fashion aspects. The specifically selected dye(s) may therefore vary, depending on the intended effects and requirements.

The invention claimed is:
1. Photochromic naphthopyrans according to formula (I) or (II) below:

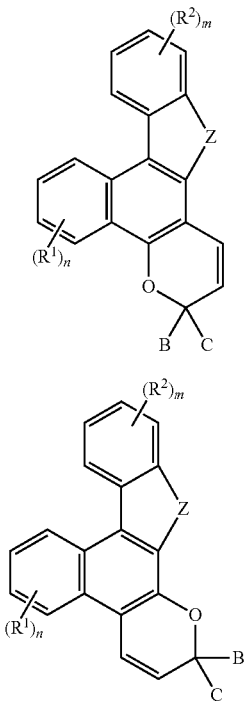

wherein
the radicals $R^1$ and $R^2$ are each independently a substituent selected from the group α, consisting of a hydrogen atom, a ($C_1$-$C_6$)-alkyl radical, a ($C_1$-$C_6$)-thioalkyl radical, a ($C_3$-$C_7$)-cycloalkyl radical which may have one or more heteroatoms such as O or S, a ($C_1$-$C_6$)-alkoxy radical, an hydroxyl group, a trifluoromethyl group, bromine, chlorine, fluorine, an unsubstituted, monosubstituted or disubstituted phenyl, phenoxy, benzyl, benzyloxy, naphthyl or naphthoxy radical, wherein the substituents in turn may be selected from the group α; or
two radicals $R^1$ and/or two radicals $R^2$ each independently form an unsubstituted, monosubstituted or disubstituted benzo, pyrido, benzofuro or benzothieno ring fused to the base structure, the substituents of which may be selected from the group α;
Z is selected from —$CR^{10}R^{11}$—, —O—, —S—, —NPh—, —N($C_1$-$C_6$)alkyl, —O—$CR^{10}R^{11}$—, —$CR^{10}R^{11}$—O—, —S—$CR^{10}R^{11}$—, —$CR^{10}R^{11}$—S—, —$CR^{10}R^{11}$—$CR^{10}R^{11}$—, —$CR^{10}$=N— or —$CR^{10}$=$CR^{11}$—, where the substituents $R^{10}$ and $R^{11}$ may be selected from the group α;
or Z, incorporating the spiro-carbon atom, is a 3- to 8-membered carbomonocyclic or heteromonocyclic ring which may optionally bear one or more substituents from the group α, and to which one to three aromatic or heteroaromatic ring systems may be fused, wherein the ring system(s) are independently selected from the group β consisting of benzene, naphthalene, phenanthrene, pyridine, quinoline, furan, thiophene, pyrrole, benzofuran, benzothiophene, indole and carbazole, which in turn may be substituted with one or more substituents selected from the group α;
or Z, incorporating the spiro-carbon atom, is a 7- to 12-membered carbobicyclic ring or a 7- to 12-membered carbotricyclic ring, which in turn may have one, two, three or four substituents selected from the group α, and wherein
B is selected from one of the following groups a) or b), wherein
a) is a mono-, di- and trisubstituted aryl radical, wherein the aryl radical is phenyl, naphthyl or phenanthryl;
b) is an un-, mono- and disubstituted heteroaryl radical, wherein the heteroaryl radical is pyridyl, furanyl, thienyl, benzofuranyl, benzothienyl, 1,2,3,4-tetrahydrocarbazolyl and julolidinyl;
wherein the substituents of the aryl and heteroaryl radicals in a) and b) are those selected from the group α or the group χ consisting of hydroxy, amino, mono-($C_1$-$C_6$)-alkylamino, di-($C_1$-$C_6$)-alkylamino, and on the phenyl ring un-, mono- or disubstituted phenethenyl, un-, mono- or disubstituted (phenylimino)methylene, un-, mono- or disubstituted (phenylmethylene)imino and un-, mono- or disubstituted mono- and diphenylamino, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono- or disubstituted 1,2,3,4-tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenz[b,f]azepinyl, wherein the substituent(s) in turn may each independently be selected from ($C_1$-$C_6$)-alkyl, ($C_1$-$C_6$)-alkoxy, bromine, chlorine or fluorine;
or wherein two directly adjacent substituents of the aryl and heteroaryl radicals in a) and b) are a V—($CR^{12}R^{13}$)$_p$—W moiety, where p is 1, 2 or 3, $R^{12}$ and $R^{13}$ may be hydrogen, methyl or phenyl and V and W may independently be oxygen, sulfur, N—($C_1$-$C_6$)-alkyl, N—$C_6H_5$, $CH_2$, $C(CH_3)_2$ or $C(C_6H_5)_2$, wherein two or more adjacent carbon atoms in this V—($CR^{12}R^{13}$)$_p$—W moiety each independently can also be part of a fused benzo ring system, which in turn may have one or more substituents selected from the group α or the group χ;
and wherein the aryl radical or heteroaryl radical of the group B in the two positions ortho to the point of attachment to the pyran ring has no substituent other than hydrogen, and wherein C is a substituent of the following structure, C = 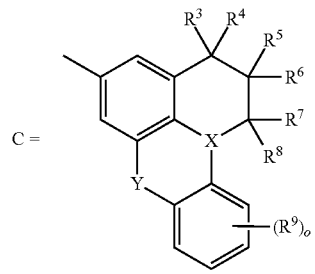

wherein $R^9$ is defined as $R^1$ and $R^2$, where m, n and o are independently an integer from 1 to 4;
wherein $R^3$ to $R^8$ are each independently a substituent selected from the group α; or
$R^3$ together with $R^4$ or $R^5$ together with $R^6$ or $R^7$ together with $R^8$ independently form, with the respective common carbon atom, a 3- to 8-membered carbomonocyclic or heteromonocyclic ring, which optionally bears one or more substituents from the group α, and to which one to three aromatic or heteroaromatic ring systems may be fused, wherein the ring system(s) are independently selected from the group β consisting of benzene, naphthalene, phenanthrene, pyridine, quinoline, furan, thiophene, pyrrole, benzofuran, benzothiophene, indole and carbazole, which in turn may be substituted with one or more substituents selected from the group α; or four adjacent radicals $R^3$ to $R^6$ or $R^5$ to $R^8$ form an un-, mono- or disubstituted benzo or pyrido ring, fused to the base structure, the substituents of which may be selected from the group α;

where X is N or $CR^{14}$, wherein $R^{14}$ is selected from the group consisting of hydrogen, a $(C_1$-$C_6)$-alkyl radical and un-, mono- and disubstituted phenyl, the substituents of which are selected from the group α; and where Y is O, S, $NR^{15}$, $CR^{15}R^{16}$ or $CR^{15}R^{16}$—$CR^{15}R^{16}$, wherein $R^{15}$ and $R^{16}$ may each be selected as $R^{14}$, or the two radicals $R^{15}$ and $R^{16}$, together with the common carbon atom, form a 3- to 8-membered carbomonocyclic or heteromonocyclic ring, which optionally bears one or more substituents from the group α, and to which one to three aromatic or heteroaromatic ring systems may be fused, wherein the ring system(s) are independently selected from the group β consisting of benzene, naphthalene, phenanthrene, pyridine, quinoline, furan, thiophene, pyrrole, benzofuran, benzothiophene, indole and carbazole, which in turn may be substituted with one or more substituents selected from the group α.

2. The photochromic naphthopyrans as claimed in claim 1 having the formula (I).

3. The photochromic naphthopyrans as claimed in claim 1 having the following general formulae (III), (IV) and (V):

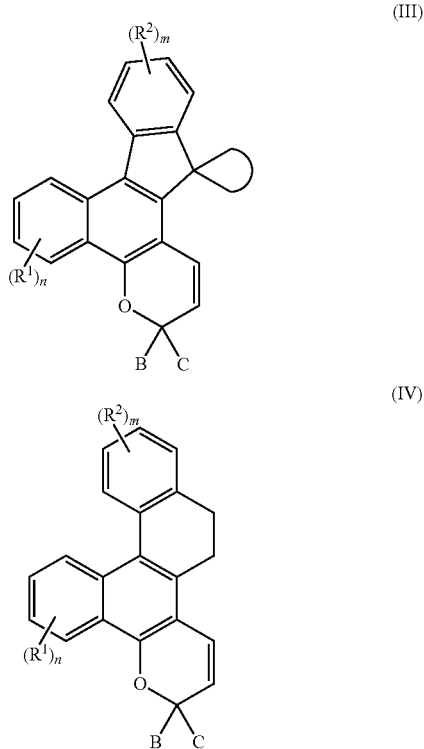

(III)

(IV)

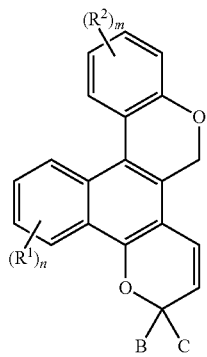

(V)

wherein all radicals are as defined above and wherein the spiro-ring in formula (III), incorporating the spiro-carbon atom, is a 5- to 8-membered carbocyclic ring, which optionally bears one or more substituents from the group α, and to which one to three benzene rings may be fused, which in turn may be substituted with one or more substituents selected from the group α.

4. The photochromic naphthopyrans as claimed in claim 1, wherein the radical B is selected from the group a).

5. The photochromic naphthopyrans as claimed in claim 1, wherein X is N in the radical C.

6. The photochromic naphthopyrans as claimed in claim 1, wherein Y is $CR^{15}R^{16}$ or $CR^{15}R^{16}$—$CR^{15}R^{16}$ in the radical C, wherein $R^{15}$ and $R^{16}$ are as defined above.

7. The photochromic naphthopyrans as claimed in claim 1, wherein $R^3$ to $R^8$ are each independently a substituent selected from the group α.

8. The photochromic naphthopyrans as claimed in claim 1, wherein $R^3$ and $R^4$ are each independently a substituent selected from the group α; and, at the same time, the four radicals $R^5$ to $R^8$ together form an un-, mono- or disubstituted benzo or pyrido ring, fused to the base structure, the substituents of which may be selected from the group α.

9. The photochromic naphthopyrans as claimed in claim 1, wherein the radical C has the following structures

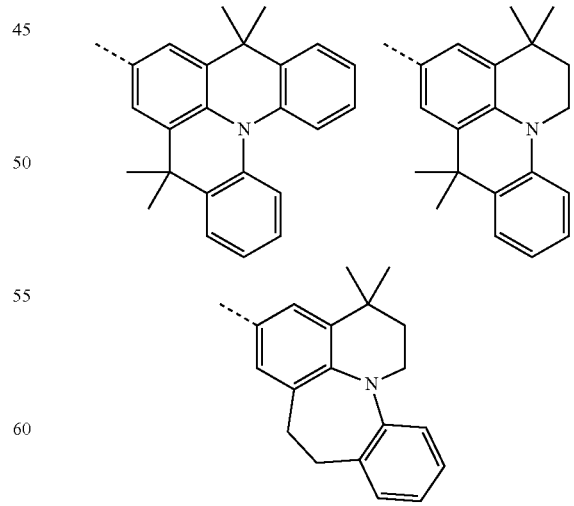

10. The photochromic naphthopyrans as claimed in claim 1, wherein two radicals $R^2$ in the above formulae (I)-(V) form an un-, mono- or disubstituted benzo, pyrido, benzofuro or benzothieno ring, fused to the base structure and the substituents of which may be selected from the group α.

11. The photochromic naphthopyrans as claimed in-claim 1, wherein two radicals $R^2$, mutually in the ortho position, present in the above formulae (I)-(V), are a benzofuro fused attachment.

12. The photochromic naphthopyrans as claimed in claim 1, wherein Z is selected from —$CR^{10}R^{11}$—, —O—$CR^{10}R^{11}$—, —O—, —$CR^{10}R^{11}$ or —$CR^{10}$=$CR^{11}$—, wherein the substituents $R^{10}$ and $R^{11}$ are selected from the group α.

13. A plastic material comprising one or more of the photochromic naphthopyrans as claimed in claim 1.

14. The plastic material of claim 13, wherein the plastic material is an ophthalmic lens.

* * * * *